US012667342B2

(12) United States Patent
Jiang et al.

(10) Patent No.: US 12,667,342 B2
(45) Date of Patent: Jun. 30, 2026

(54) SYSTEM AND METHOD FOR AUTOMATICALLY ACQUIRING AND ROTATING AN ULTRASOUND VOLUME BASED ON A LOCALIZED TARGET STRUCTURE

(71) Applicant: GE Precision Healthcare LLC, Wauwatosa, WI (US)

(72) Inventors: Hongjian Jiang, Wuxi (CN); Olivier Gerard, Oslo (NO); Nuno Almeida, Oslo (NO); Zhiqiang Jiang, Wuxi (CN); Jinchuan Wang, Wuxi (CN)

(73) Assignee: GE Precision Healthcare LLC, Waukesha, WI (US)

( * ) Notice: Subject to any disclaimer, the term of this patent is extended or adjusted under 35 U.S.C. 154(b) by 61 days.

(21) Appl. No.: 18/089,013

(22) Filed: Dec. 27, 2022

(65) Prior Publication Data

US 2024/0206852 A1 Jun. 27, 2024

(51) Int. Cl.
A61B 8/00 (2006.01)
A61B 8/08 (2006.01)
A61B 8/14 (2006.01)

(52) U.S. Cl.
CPC ............ A61B 8/5238 (2013.01); A61B 8/085 (2013.01); A61B 8/145 (2013.01); A61B 8/465 (2013.01); A61B 8/466 (2013.01); A61B 8/483 (2013.01)

(58) Field of Classification Search
CPC ....... A61B 8/5238; A61B 8/085; A61B 8/145; A61B 8/465; A61B 8/466; A61B 8/483
See application file for complete search history.

(56) References Cited

U.S. PATENT DOCUMENTS

| | | | |
|---|---|---|---|
| 10,835,210 B2 | 11/2020 | Ralovich et al. | |
| 2011/0301463 A1* | 12/2011 | Fujii ...................... | A61B 8/463 |
| | | | 600/443 |
| 2016/0173770 A1* | 6/2016 | Fosodeder ........... | A61B 8/5207 |
| | | | 348/77 |
| 2016/0287214 A1* | 10/2016 | Ralovich ................ | A61B 8/469 |
| 2018/0242950 A1* | 8/2018 | Abe ........................ | G06T 7/248 |
| 2020/0202635 A1* | 6/2020 | Liang ........................ | G06T 7/73 |

FOREIGN PATENT DOCUMENTS

CN 112330822 A 2/2021

* cited by examiner

*Primary Examiner* — Andrew W Begeman
(74) *Attorney, Agent, or Firm* — McAndrews, Held & Malloy, Ltd.; Daniel Bissing; David Bates

(57) ABSTRACT

Systems and methods for automatically acquiring and rotating an ultrasound volume based on a localized target structure are provided. The method includes performing a first ultrasound image acquisition and automatically detecting and tracking one or more anatomical structures in the first ultrasound image acquisition. The method includes presenting a region of interest surrounding each of the one or more anatomical structures in the first ultrasound image acquisition. The method includes performing a second ultrasound image acquisition of the region of interest to acquire a volume. The method includes estimating a pose of the one or more anatomical structures within the volume and calculating a rotation of the volume from the estimated pose to a pre-defined orientation of the one or more anatomical structures. The method includes presenting a rendering of the volume automatically rotated to the pre-defined orientation.

20 Claims, 9 Drawing Sheets

900

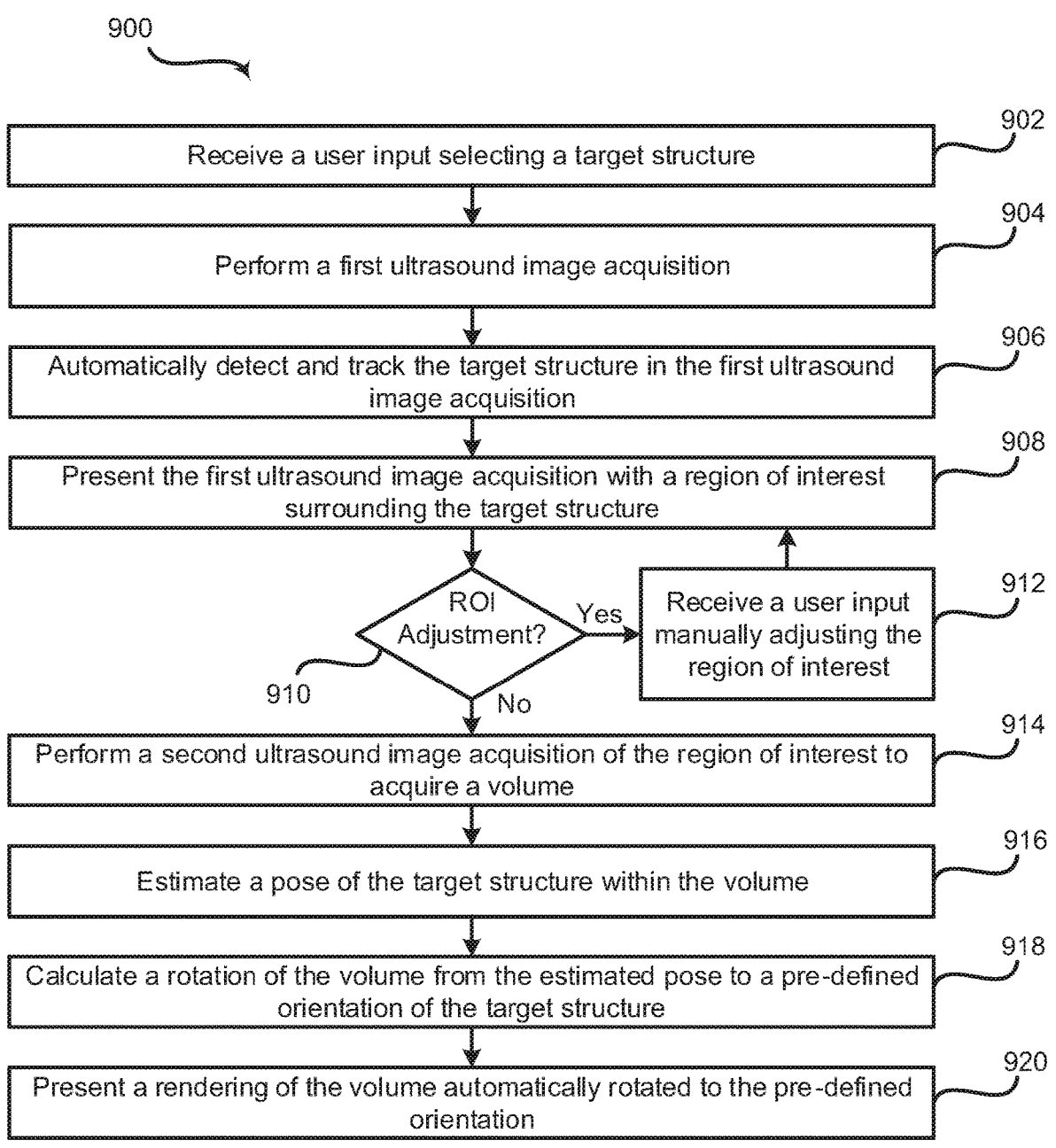

902 Receive a user input selecting a target structure

904 Perform a first ultrasound image acquisition

906 Automatically detect and track the target structure in the first ultrasound image acquisition 908 Present the first ultrasound image acquisition with a region of interest surrounding the target structure 910 ROI Adjustment?

Yes

912 Receive a user input manually adjusting the region of interest

No

914 Perform a second ultrasound image acquisition of the region of interest to acquire a volume 916 Estimate a pose of the target structure within the volume 918 Calculate a rotation of the volume from the estimated pose to a pre-defined orientation of the target structure 920 Present a rendering of the volume automatically rotated to the pre-defined orientation

FIG. 8

1002 Perform a first ultrasound image acquisition

1004 Automatically detect and track one or more anatomical structures in the first ultrasound image acquisition 1006 Present the first ultrasound image acquisition with a region of interest surrounding each of the one or more anatomical structures 1008 Receive a user input selecting at least one target structure corresponding to at least one of the one or more anatomical structures 1010 Redefine the region of interest to surround the selected at least one target structure 1012 Perform a second ultrasound image acquisition of the region of interest to acquire a volume 1014 Estimate a pose of the target structure within the volume 1016 Calculate a rotation of the volume from the estimated pose to a pre-defined orientation of the target structure 1018 Present a rendering of the volume automatically rotated to the pre-defined orientation

SYSTEM AND METHOD FOR AUTOMATICALLY ACQUIRING AND ROTATING AN ULTRASOUND VOLUME BASED ON A LOCALIZED TARGET STRUCTURE

FIELD

Certain embodiments relate to ultrasound imaging. More specifically, certain embodiments relate to a method and system for automatically acquiring and rotating an ultrasound volume based on a localized target structure.

BACKGROUND

Ultrasound imaging is a medical imaging technique for imaging organs and soft tissues in a human body. Ultrasound imaging uses real time, non-invasive high frequency sound waves to produce two-dimensional (2D), three-dimensional (3D), and/or four-dimensional (4D) (i.e., real-time/continuous 3D images) images.

Four-dimensional (4D) ultrasound imaging (i.e., real-time/continuous 3D ultrasound imaging) is a powerful tool for real-time heart (e.g., muscle and chambers) movement visualization. However, current methods and ultrasound systems for acquiring a focused 3D/4D volume of target structures are complicated (i.e., many manual steps) and require a great sense of space and familiarity with the workflow of an ultrasound scanner.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for automatically acquiring and rotating an ultrasound volume based on a localized target structure, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

BRIEF DESCRIPTION OF SEVERAL VIEWS OF THE DRAWINGS

FIG. 8 is a flow chart illustrating exemplary steps that may be utilized for automatically acquiring and rotating an ultrasound volume based on a localized target structure, in accordance with various embodiments.

FIG. 9 is a flow chart illustrating exemplary steps that may be utilized for automatically acquiring and rotating an ultrasound volume based on a localized target structure, in accordance with various embodiments.

DETAILED DESCRIPTION

Figure 1:
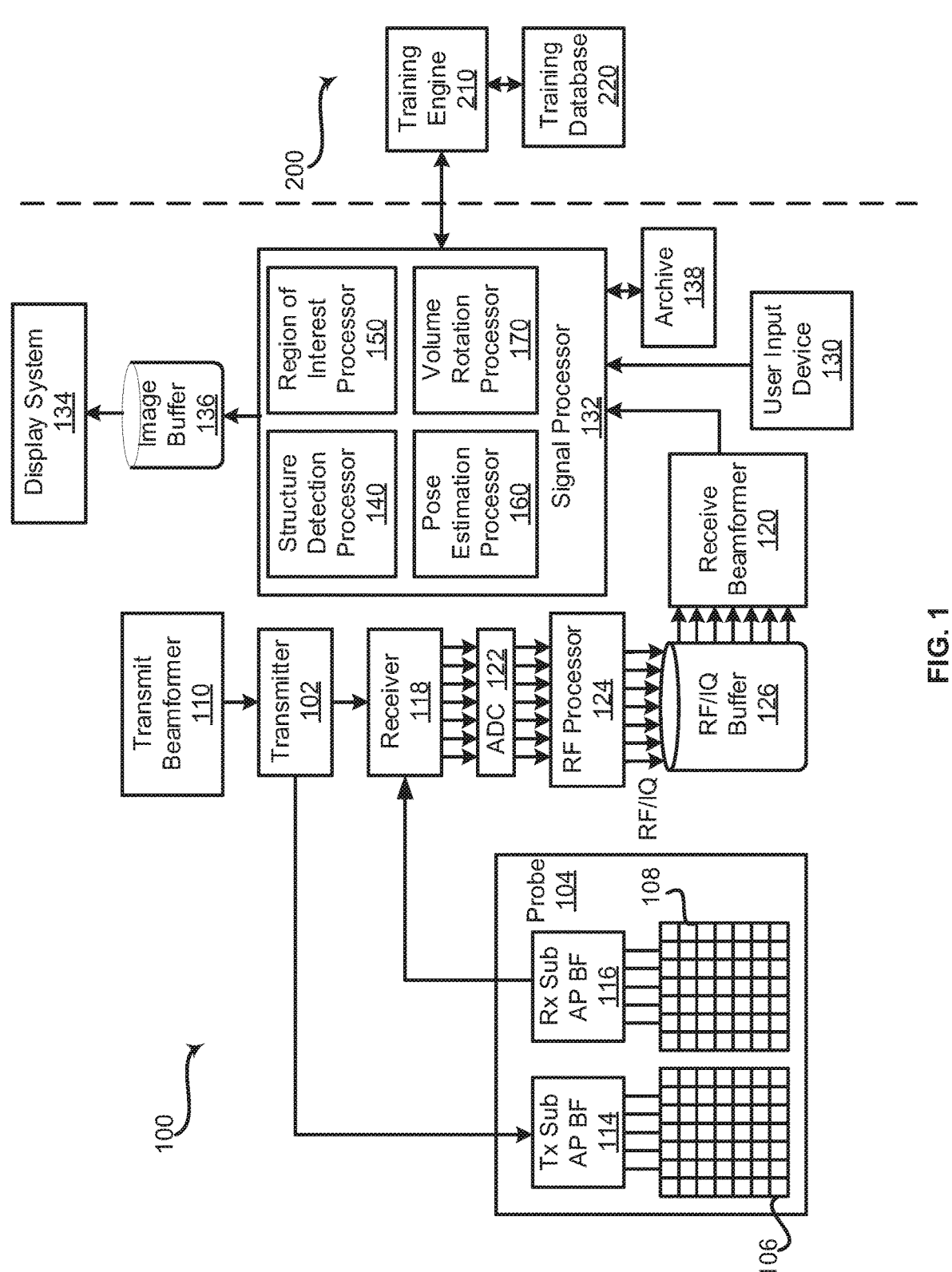
FIG. 1 is a block diagram of an exemplary ultrasound system that is operable to automatically acquire and rotate an ultrasound volume based on a localized target structure, in accordance with various embodiments.

Certain embodiments may be found in a method and system for automatically acquiring and rotating an ultrasound volume based on a localized target structure. Aspects of the present disclosure have the technical effect of automatically providing real-time feedback regarding the presence or absence of a target structure and its location in a live ultrasound scan. Various embodiments have the technical effect of allowing an ultrasound operator to manually adjust a region of interest surrounding a selected target structure being automatically tracked by an ultrasound system. Certain embodiments have the technical effect of automatically acquiring an ultrasound volume (e.g., 3D/4D) focused on the selected target structure(s). Aspects of the present disclosure provide the technical effect of automatically rotating an ultrasound volume (e.g., 3D/4D) to a pre-defined orientation associated with the selected target structure(s). Various embodiments have the technical effect of automatically providing real-time feedback regarding the existence and locations of all anatomical structures in a live ultrasound scan with multiple target structure selection options, such as selectable regions of interest and selectable buttons on a touch panel corresponding with each of the automatically detected anatomical structures.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment." and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, Contrast Enhanced Ultrasound (CEUS), and/or sub-modes of B-mode and/or CF such as Harmonic Imaging, Shear Wave Elasticity Imaging (SWEI), Strain Elastography, TVI, PDI, B-flow, MVI, UGAP, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to automatically acquire and rotate an ultrasound volume based on a localized target structure, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. Additionally and/or alternatively, the ultrasound probe 104 may be a mechanically wobbling ultrasound probe 104, which may comprise a one dimensional (1D) array of piezoelectric elements mounted on a transducer assembly movable in a single plane. For example, the transducer assembly may be movable approximately 120 to 150 degrees by a motor driving gears, belts, and/or rope to pivot an axis or hub of the transducer assembly. In certain embodiments, the ultrasound probe 104 is a transesophageal ultrasound probe. The ultrasound probe 104 may comprise a group of transmit transducer elements 106 and a group of receive transducer elements 108, that normally constitute the same elements. The group of transmit transducer elements 106 may emit ultrasonic signals through oil and a probe cap and into a target. In a representative embodiment, the ultrasound probe 104 may be operable to acquire ultrasound image data covering at least a substantial portion of an anatomy, such as an ovary or any suitable anatomical structure. In an exemplary embodiment, the ultrasound probe 104 may be operated in a volume acquisition mode, where the transducer assembly of the ultrasound probe 104 acquires a plurality of parallel 2D ultrasound slices forming an ultrasound volume.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select target structures for automatic detection and tracking, modify a region of interest, select regions of interest and/or activatable buttons corresponding with regions of interest used to acquire a focused/zoomed volume, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a structure detection processor 140, a region of interest processor 150, a pose estimation processor 160, and a volume rotation processor 170. The signal processor 132 may be capable of receiving input information from a user input device 130 and/or archive 138, generating an output displayable by a display system 134, and manipulating the output in response to input information from a user input device 130, among other things. The signal processor 132, structure detection processor 140, region of interest processor 150, pose estimation processor 160, and volume rotation processor 170 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a structure detection processor 140 that comprises suitable logic, circuitry, interfaces and/or code that may be operable to analyze acquired ultrasound images and/or volumes to detect a presence and location of anatomical structures in the ultrasound images and/or volumes. In this regard, the structure detection processor 140 may include, for example, image analysis algorithms, one or more deep neural networks (e.g., a convolutional neural network such as u-net) and/or may utilize any suitable form of image analysis techniques, artificial intelligence, or machine learning processing functionality configured to detect and localize anatomical structures in ultrasound images and/or volumes. Additionally and/or alternatively, the image analysis techniques, artificial intelligence, or machine learning processing functionality configured to detect and localize anatomical structures in ultrasound images and/or volumes may be provided by a different processor or distributed across multiple processors at the ultrasound system 100 and/or a remote processor communicatively coupled to the ultrasound system 100. For example, the structure detection and localization functionality may be provided as a deep neural network that may be made up of, for example, an input layer, an output layer, and one or more hidden layers in between the input and output layers. Each of the layers may be made up of a plurality of processing nodes that may be referred to as neurons. For example, the structure detection and localization functionality may include an input layer having a neuron for each pixel of an ultrasound image and/or voxel of an ultrasound volume. The output layer may have a neuron corresponding to each heart muscle, heart chamber, and/or any suitable anatomical structure. Each neuron of each layer may perform a processing function and pass the processed ultrasound image information to one of a plurality of neurons of a downstream layer for further processing. As an example, neurons of a first layer may learn to recognize edges of structure in the obtained ultrasound image and/or volume. The neurons of a second layer may learn to recognize shapes based on the detected edges from the first layer. The neurons of a third layer may learn positions of the recognized shapes relative to landmarks in the obtained ultrasound image and/or volume. The processing performed by the deep neural network may identify anatomical structures and the location of the anatomical structures in the obtained ultrasound images and/or volume with a high degree of probability.

Figure 2:
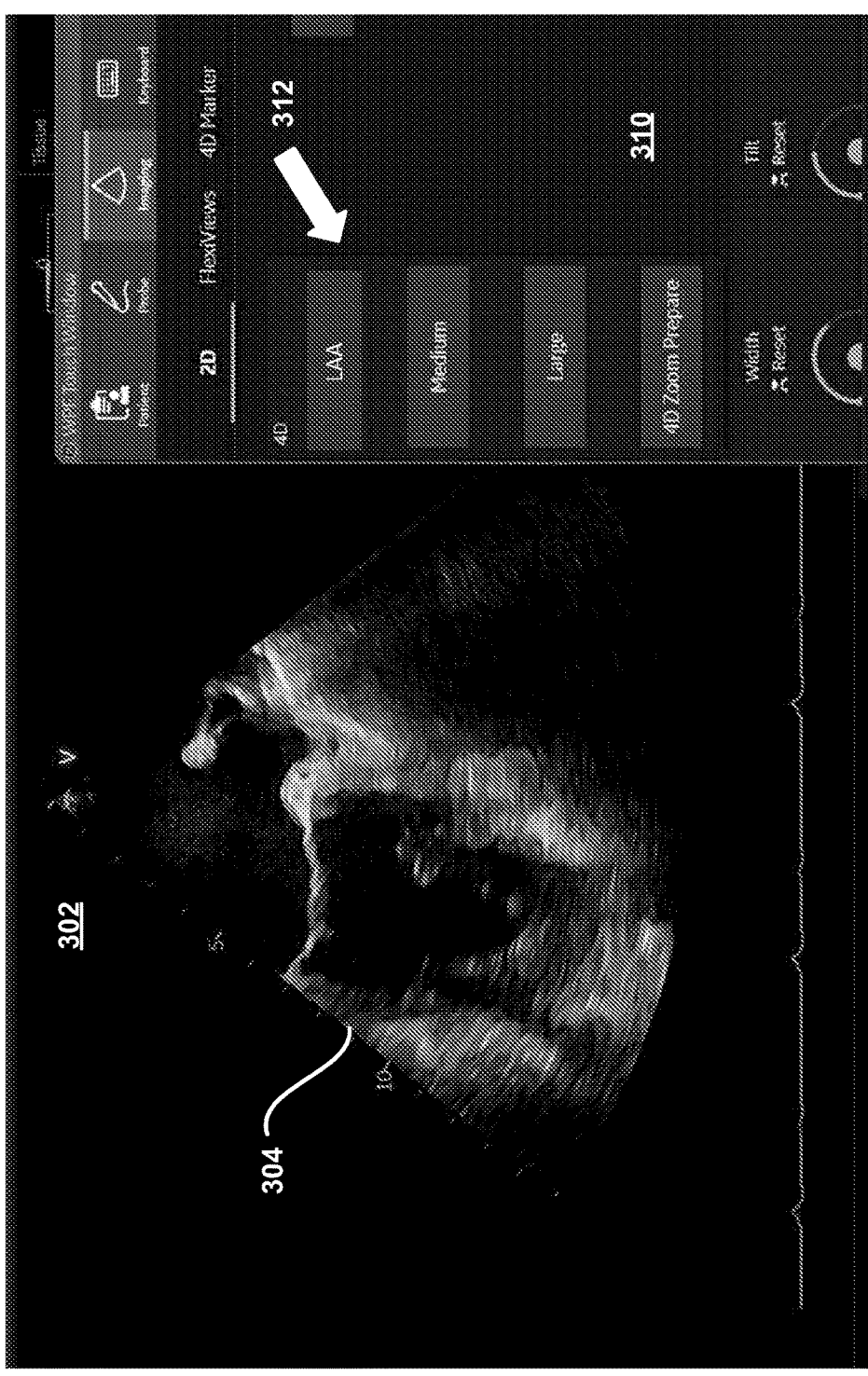
FIG. 2 is an exemplary display of a two-dimensional (2D) ultrasound image and an interface for selecting a target structure, in accordance with various embodiments.

In an exemplary embodiment, the structure detection processor 140 may be configured to analyze the ultrasound images and/or volume to detect and localize a selected target structure. For example, the structure detection processor 140 may be configured to receive a user input selecting a target structure prior to performing a first ultrasound image acquisition and analyzing the ultrasound image and/or volume of the first ultrasound image acquisition to detect and localize the selected target structure. FIG. 2 is an exemplary display 300 of a two-dimensional (2D) ultrasound image 304 and an interface 310 for selecting a target structure 312, in accordance with various embodiments. Referring to FIG. 2, the display 300 includes an image display portion 302 comprising an ultrasound image 304, and an interface 310 for selecting a target structure 312. The interface 310 may be provided on a main display of the display system 134 with the image display portion 302 as shown in FIG. 2 and/or may be provided on a touch panel of the display system 134. The interface 310 may include a list of one or more selectable anatomical structures 312. The structure detection processor 140 may be configured to receive a user input selecting a target structure 312, such as a left atrial appendage (LAA) as shown in FIG. 2. The user input selecting the target structure 312 may trigger a first ultrasound image acquisition by the ultrasound probe 104. The first ultrasound image acquisition may be a 2D image acquisition, such as acquiring 2D biplane ultrasound images for analysis by the structure detection processor 140. Additionally and/or alternatively, the first ultrasound image acquisition may be a volume acquisition. The structure detection processor 140 may be configured to analyze the acquired volume to detect and localize the selected target structure 312. The detected and localized target structure 312 may be provided by the structure detection processor 140 to the region of interest processor 150. Additionally and/or alternatively, the detected and localized target structure 312 may be stored at archive 138 and/or any suitable computer readable medium.

Referring again to FIG. 1, the structure detection processor 140 may be configured to analyze the ultrasound images and/or volume to detect and localize all anatomical structures present in the ultrasound images and/or volume. For example, the structure detection processor 140 may be configured to analyze an ultrasound image and/or volume of a first ultrasound image acquisition to detect and localize all anatomical structures present in the ultrasound images and/or volume without and/or prior to receiving a selected target structure. The detected and localized anatomical structures may be provided by the structure detection processor 140 to the region of interest processor 150. Additionally and/or alternatively, the detected and localized anatomical structures may be stored at archive 138 and/or any suitable computer readable medium.

The signal processor 132 may include a region of interest processor 150 that comprises suitable logic, circuitry, interfaces and/or code that may be operable to cause a display system 134 to present a first ultrasound image acquisition with a region of interest surrounding a selected target structure detected and localized by the structure detection processor 140. For example, the region of interest processor 150 may be configured to receive from the structure detection processor 140, or retrieve from the archive 138 and/or any suitable data storage medium, the identity and location of a selected target structure. The region of interest processor 150 may be configured to identify the localized selected target structure by overlaying a bounding box, colorizing pixels, and/or any suitable identification technique. The first ultrasound image acquisition having the identified region(s) of interest may include a 2D image, 2D biplane images, 2D biplane image slices extracted from a volume, a rendered volume, and/or any suitable ultrasound image and/or volume rendering (i.e., 2D projection of 3D/4D volume image data).

In various embodiments, the region of interest processor 150 may comprise suitable logic, circuitry, interfaces, and/or code that may be operable to modify the region of interest in response to a user input. For example, in response to the region of interest processor 150 causing the display system 134 to present the first ultrasound image acquisition with the region of interest surrounding a selected target structure, an ultrasound operator may provide an input via the user input device 130 and/or touchscreen display 130, 134 to modify a size and/or location of the displayed region of interest. The region of interest processor 150 may be configured to initiate a second ultrasound image acquisition of the region of interest automatically and/or in response to a user input. For example, the region of interest processor 150 may automatically initiate the second ultrasound image acquisition by the ultrasound probe 104 if a user input is not received to modify the position and/or size of the region of interest in a predetermined period of time. As another example, the region of interest processor 150 may be configured to initiate the second ultrasound image acquisition by the ultrasound probe 104 in response to a user input. In addition, the region of interest processor 150 may be configured to initiate the second ultrasound image acquisition by the ultrasound probe 104 in response to a predetermined period of time expiring after the region of interest has been modified and/or in response to a user input after the region of interest has been modified.

Figure 3:
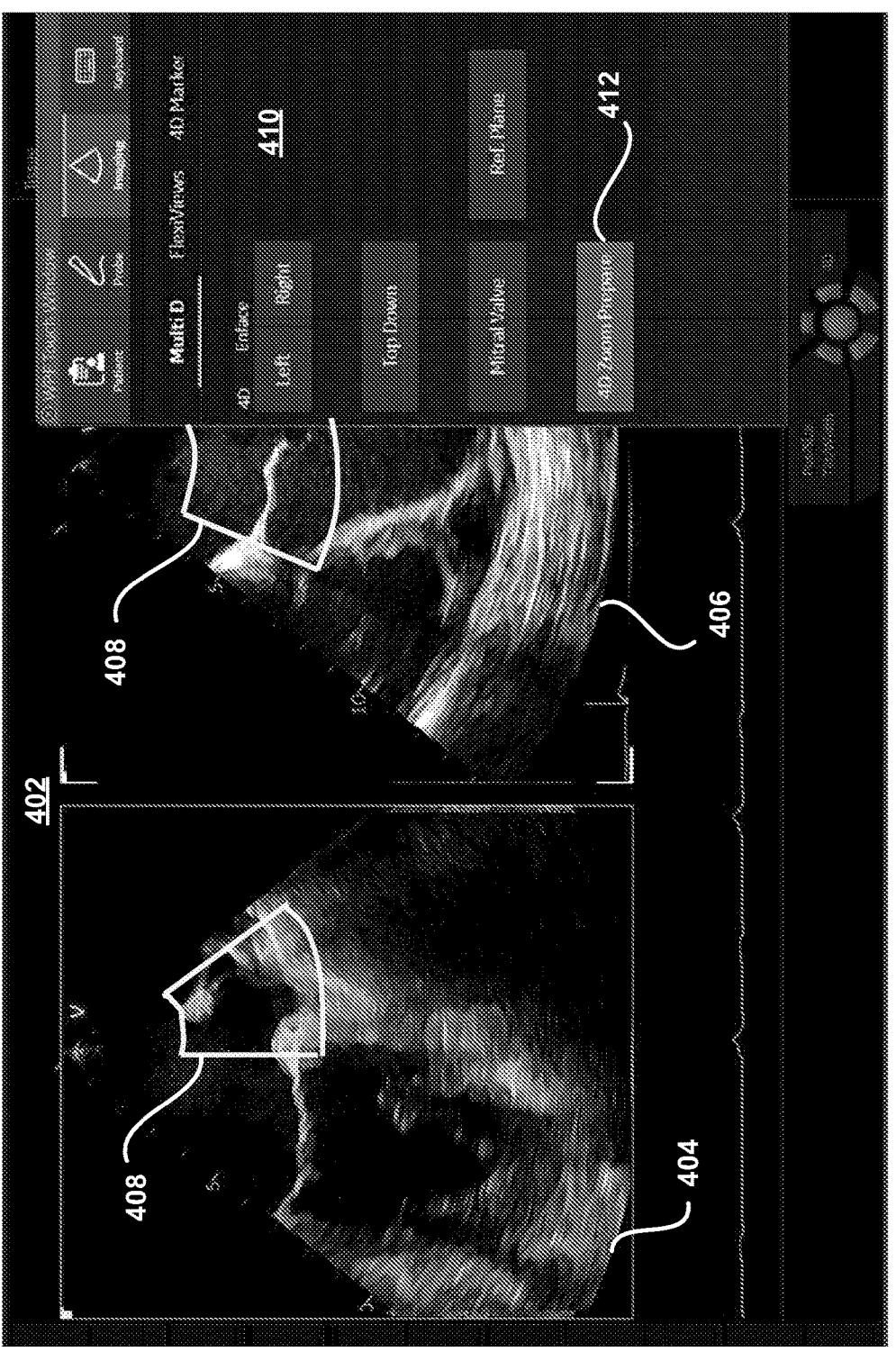
FIG. 3 is an exemplary display of a modifiable region of interest superimposed on biplane images to surround a selected target structure automatically detected in the biplane images, in accordance with various embodiments.

FIG. 3 is an exemplary display 400 of a modifiable region of interest 408 superimposed on biplane images 404, 406 to surround a selected target structure automatically detected in the biplane images 404, 406, in accordance with various embodiments. Referring to FIG. 3, the display 400 comprises an image display portion 402 comprising biplane ultrasound images 404, 406, each of which is overlaid with a region of interest 408, and an interface 410 with a button 412 for initiating a second ultrasound image acquisition. The interface 410 may be provided on a main display of the display system 134 with the image display portion 402 as shown in FIG. 3 and/or may be provided on a touch panel of the display system 134. The interface 410 may include a button 412 for initiating a second ultrasound image acquisition of an ultrasound volume (3D/4D) focused (i.e., zoomed) to the region of interest 408. The 2D biplane images 404, 406 may additionally and/or alternatively be a single 2D image, a rendering of a volume (3D/4D), 2D biplane image slices extracted from a volume (3D/4D), and/or any suitable ultrasound images. The region of interest 408 may be presented as a bounding box, colorized pixels, and/or any suitable identifier. The region of interest 408 may be modifiable by user input received via the user input device 130 and/or touchscreen display 130, 134 to adjust a position and/or size of the region of interest 408. In an exemplary embodiment, the region of interest processor 150 may automatically initiate a second ultrasound image acquisition (e.g., 3D/4D volume acquisition) by the ultrasound probe 104 focused/zoomed on the region of interest 408 if a user input is not received to modify the position and/or size of the region of interest 408 within a pre-defined time period. The region of interest processor 150 may be configured to initiate the second ultrasound image acquisition (e.g., 3D/4D volume acquisition) by the ultrasound probe 104 in response to a user input, such as a selection of the 4D Zoom Prepare button 412 in the interface 410. In addition, the region of interest processor 150 may be configured to initiate the second ultrasound image acquisition (e.g., 3D/4D volume acquisition) by the ultrasound probe 104 in response to expiration of the pre-defined time period after the region of interest 408 has been modified and/or in response to selection of the 4D Zoom Prepare 412 button in the interface 410 after the region of interest 408 has been modified.

Referring again to FIG. 1, the region of interest processor 150 may comprise suitable logic, circuitry, interfaces and/or code that may be operable to cause a display system 134 to present a first ultrasound image acquisition with regions of interest surrounding all of the anatomical structures detected and localized by the structure detection processor 140. For example, the region of interest processor 150 may be configured to receive from the structure detection processor 140, or retrieve from the archive 138 and/or any suitable data storage medium, the identity and location of all of the detected anatomical structures. The region of interest processor 150 may be configured to identify the localized anatomical structures by overlaying a bounding box, colorizing pixels, and/or any suitable identification technique. The first ultrasound image acquisition having the identified region(s) of interest may include a 2D image, 2D biplane images, 2D biplane image slices extracted from a volume, a rendered volume, and/or any suitable ultrasound image and/or volume rendering (i.e., 2D projection of 3D/4D volume image data).

In a representative embodiment, the region of interest processor 150 may comprise suitable logic, circuitry, interfaces, and/or code that may be operable to redefine the region of interest in response to a user input selecting one or more of the regions of interest and/or anatomical structures identified in the first ultrasound image acquisition. For example, in response to the region of interest processor 150 causing the display system 134 to present the first ultrasound image acquisition with the regions of interest surrounding each of the localized anatomical structures, an ultrasound operator may provide an input via the user input device 130 and/or touchscreen display 130, 134 to select one or more of the anatomical structures. The region of interest processor 150 may be configured to redefine the regions of interest corresponding to the selected anatomical structures to form a single region of interest surrounding the selected anatomical structures. The region of interest processor 150 may be configured to initiate a second ultrasound image acquisition of the redefined region of interest automatically and/or in response to a user input. For example, the region of interest processor 150 may automatically initiate the second ultrasound image acquisition by the ultrasound probe 104 if a user input is not received to select more or fewer regions of interest to further redefine the region of interest in a predetermined period of time. As another example, the region of interest processor 150 may be configured to initiate the second ultrasound image acquisition by the ultrasound probe 104 in response to a user input.

Figure 4:
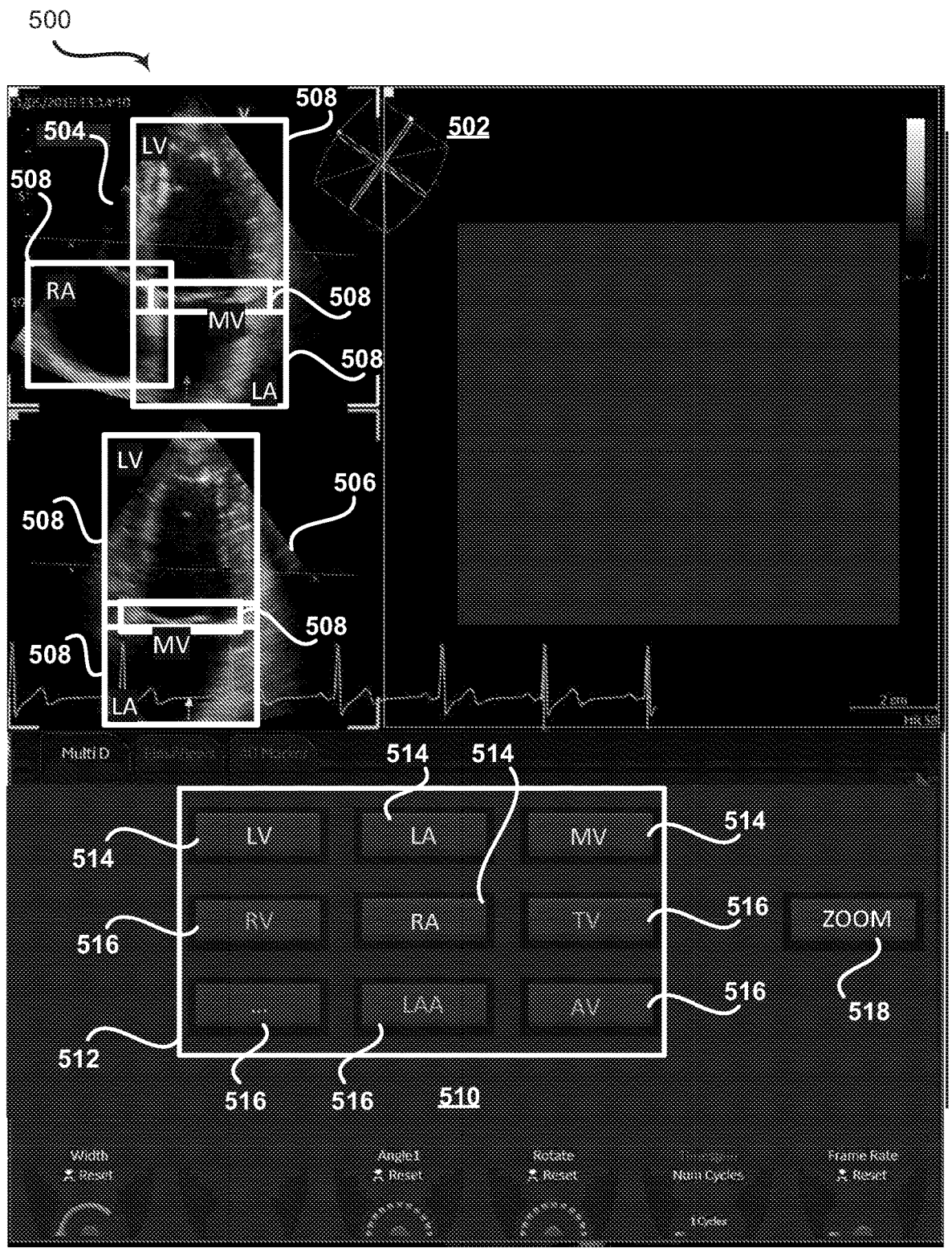
FIG. 4 is an exemplary display of selectable regions of interest surrounding automatically detected anatomical structures in biplane images and an interface for selecting one or more of the anatomical structures as at least one target structure, in accordance with various embodiments.

FIG. 4 is an exemplary display 500 of selectable regions of interest 508 surrounding automatically detected anatomical structures in biplane images 504, 506 and an interface 510 for selecting one or more of the anatomical structures 514 as at least one target structure, in accordance with various embodiments. Referring to FIG. 4, the display 500 comprises an image display portion 502 comprising biplane ultrasound images 504, 506, each of which is overlaid with region of interests 508 corresponding with each of the detected anatomical structures, and an interface 510 with a set of buttons 512 corresponding to anatomical structures and a button 518 for initiating a second ultrasound image acquisition. The 2D biplane images 504, 506 in the image display portion 502 may additionally and/or alternatively be a single 2D image, a rendering of a volume (3D/4D), 2D biplane image slices extracted from a volume (3D/4D), and/or any suitable ultrasound images. The regions of interest 508 may be presented as a bounding box, colorized pixels, and/or any suitable identifier. Each of the regions of interest 508 presented on the biplane ultrasound images 504, 506 in the image display portion 502 may be selectable to select at least one target structure for the second ultrasound image acquisition. The interface 510 may be provided on a main display of the display system 134 with the image display portion 502 and/or may be provided on a touch panel of the display system 134 as shown in FIG. 4 The set of buttons 512 at the interface 510 may comprise activatable buttons 514 corresponding with detected anatomical structures and non-activatable buttons 516 corresponding with anatomical structures not detected in the first ultrasound image acquisition. The activatable buttons 514 may be selected to select at least one target structure for the second ultrasound image acquisition. The interface 510 may include a button 518 for initiating a second ultrasound image acquisition of an ultrasound volume (3D/4D) focused (i.e., zoomed) to the selected at least one target structure.

Figure 5:
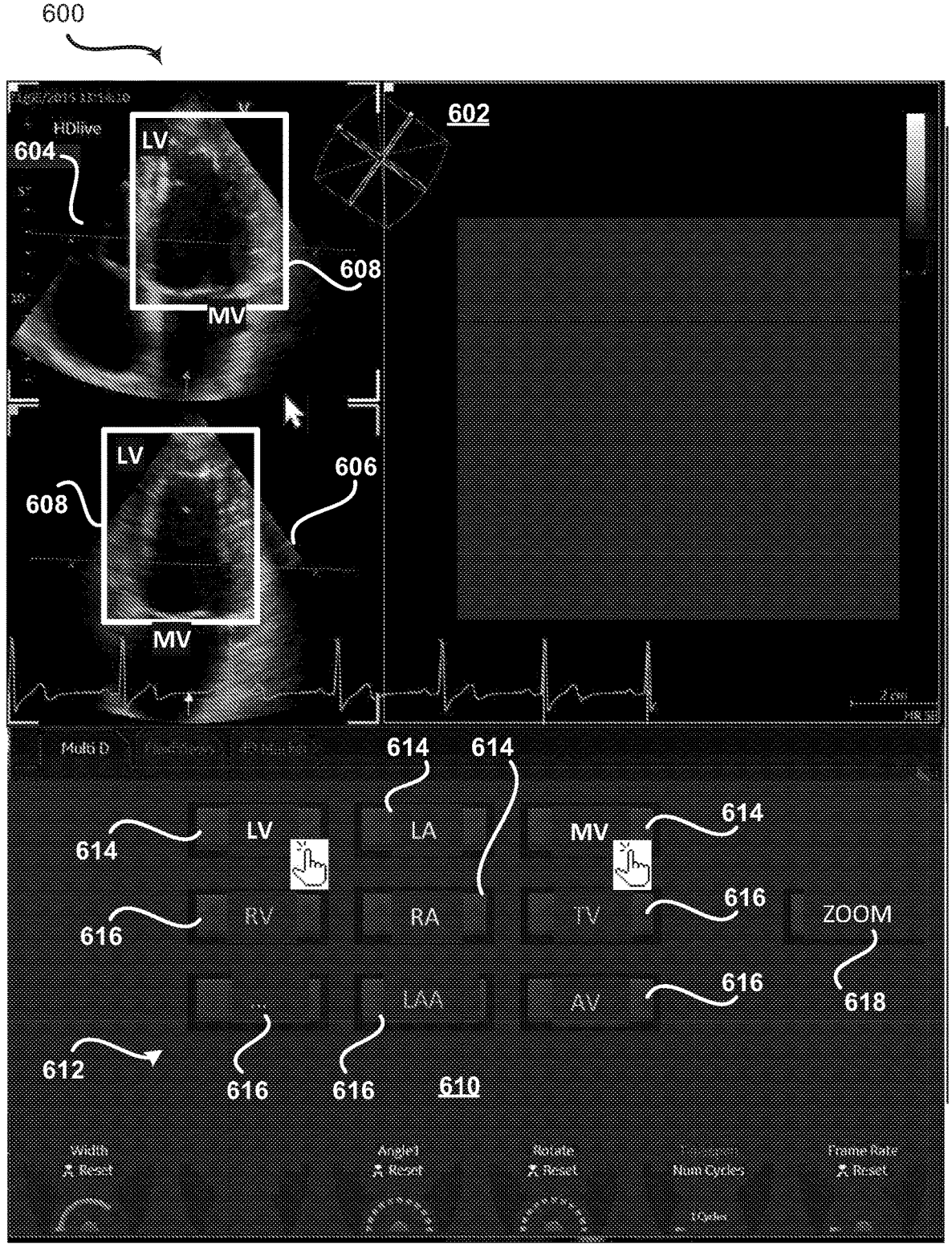
FIG. 5 is an exemplary display of a redefined region of interest surrounding the selected at least one target structure comprising one or more of the anatomical structures and an interface illustrating the selection of the one or more of the anatomical structures as the at least one target structure, in accordance with various embodiments.

FIG. 5 is an exemplary display 600 of a redefined region of interest 608 surrounding the selected at least one target structure comprising one or more of the anatomical structures and an interface 610 illustrating the selection of the one or more of the anatomical structures 614 as the at least one target structure, in accordance with various embodiments. Referring to FIG. 5, the display 600 comprises an image display portion 602 comprising biplane ultrasound images 604, 606, each of which is overlaid with a redefined region of interest 608 corresponding with at least one selected target structure, and an interface 610 with a set of buttons 612 corresponding to anatomical structures and a button 618 for initiating a second ultrasound image acquisition. The 2D biplane images 604, 606 in the image display portion 602 may additionally and/or alternatively be a single 2D image, a rendering of a volume (3D/4D), 2D biplane image slices extracted from a volume (3D/4D), and/or any suitable ultrasound images. The redefined region of interest 608 may be presented as a bounding box, colorized pixels, and/or any suitable identifier. The redefined region of interest 608 presented on the biplane ultrasound images 604, 606 in the image display portion 602 corresponds to at least one target structure for the second ultrasound image acquisition. In the example of FIG. 5, the at least one target structure is a left ventricle (LV) and a mitral valve (MV). The at least one target structure may be selected by selecting one or more of the regions of interest 508 of FIG. 4, and/or by selecting one or more of the activatable buttons 514, 614 of FIGS. 4 and 5. The interface 610 may be provided on a main display of the display system 134 with the image display portion 602 and/or may be provided on a touch panel of the display system 134 as shown in FIG. 5 The set of buttons 612 at the interface 610 may comprise activatable buttons 614 corresponding with detected anatomical structures and non-activatable buttons 616 corresponding with anatomical structures not detected in the first ultrasound image acquisition. The activatable buttons 614 may be selected to select at least one target structure for the second ultrasound image acquisition. In the example of FIG. 5, the left ventricle (LV) and mitral valve (MV) activatable buttons 614 are shown as selected. The interface 610 may include a button 618 for initiating a second ultrasound image acquisition of an ultrasound volume (3D/4D) focused (i.e., zoomed) to the redefined region of interest 608 corresponding with the at least one target structure. In an exemplary embodiment, the region of interest processor 150 may automatically initiate a second ultrasound image acquisition (e.g., 3D/4D volume acquisition) by the ultrasound probe 104 focused/zoomed on the redefined region of interest 608 if a user input changing the selected at least one target structure is not received within a pre-defined time period after the redefined region of interest 608 is displayed. The region of interest processor 150 may be configured to initiate the second ultrasound image acquisition (e.g., 3D/4D volume acquisition) by the ultrasound probe 104 in response to a user input, such as a selection of the ZOOM button 618 in the interface 610.

Referring again to FIG. 1, the signal processor 132 may include a pose estimation processor 160 that comprises suitable logic, circuitry, interfaces and/or code that may be operable to estimate a pose of the target structure within the second ultrasound image acquisition (e.g., 3D/4D volume). For example, the post estimation processor may perform image segmentation and/or any suitable image identification techniques to estimate a pose of the target structure depicted in the second ultrasound image acquisition. The pose estimation processor 160 may be configured to segment and/or otherwise identify the selected target structure within the ultrasound volume. In this regard, the pose estimation processor 160 may include, for example, image analysis algorithms, artificial intelligence algorithms, one or more deep neural networks (e.g., a convolutional neural network such as u-net) and/or may utilize any suitable form of artificial intelligence image analysis techniques or machine learning processing functionality configured to provide segmentation of selected target structure(s) and/or any suitable anatomical structure. Additionally and/or alternatively, the image analysis techniques, artificial intelligence algorithms, or machine learning processing functionality configured to segment the target structure(s) in the ultrasound volume may be provided by a different processor or distributed across multiple processors at the ultrasound system 100 and/or a remote processor communicatively coupled to the ultrasound system 100. For example, the image segmentation/identification functionality may be provided as a deep neural network that may be made up of, for example, an input layer, an output layer, and one or more hidden layers in between the input and output layers. Each of the layers may be made up of a plurality of processing nodes that may be referred to as neurons. For example, the image segmentation/identification functionality may include an input layer having a neuron for each voxel of an ultrasound volume. The output layer may have a neuron corresponding to target structure(s) and/or any suitable anatomical structure. Each neuron of each layer may perform a processing function and pass the processed ultrasound image information to one of a plurality of neurons of a downstream layer for further processing. As an example, neurons of a first layer may learn to recognize edges of structure in the obtained ultrasound volume. The neurons of a second layer may learn to recognize shapes based on the detected edges from the first layer. The neurons of a third layer may learn positions of the recognized shapes relative to landmarks in the obtained ultrasound volume. The neurons of a fourth layer may learn to determine a major axis and/or minor axis from a shape of the anatomical structure(s). The processing performed by the deep neural network may identify anatomical structures, the location of the anatomical structures, and the pose of the anatomical structures in the obtained ultrasound volume with a high degree of probability.

In an exemplary embodiment, the pose estimation processor 160 may be configured to store the estimated pose information at archive 138 and/or any suitable storage medium. The pose estimation processor 160 may be configured to provide the volume rotation processor 170 with the estimated pose information. The estimated pose information may comprise, for example, location and boundaries of anatomical structures, shape of anatomical structures, major/minor axis information, and the like.

Figure 6:
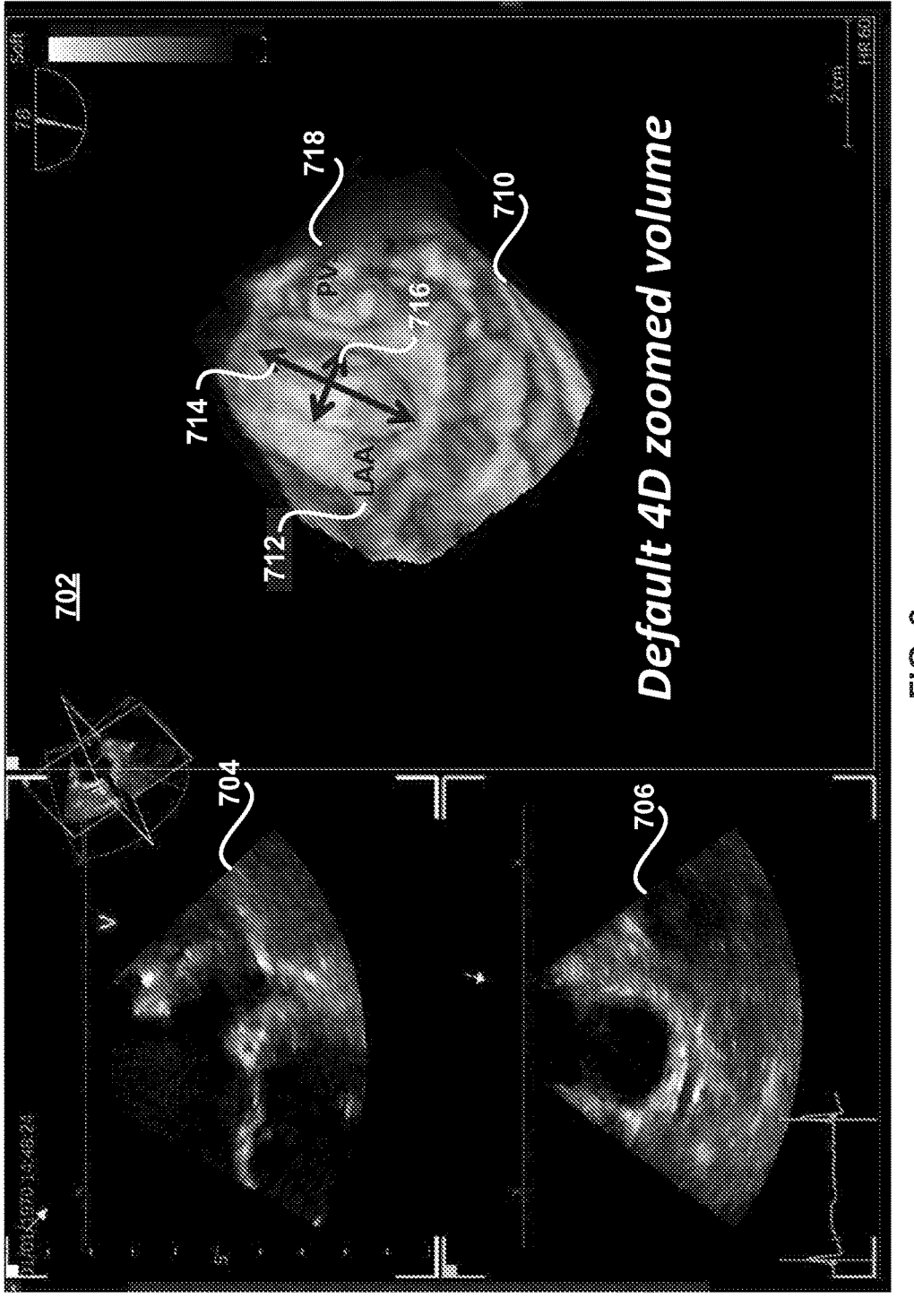
FIG. 6 is an exemplary display of biplane images and a rendering of an acquired volume of the at least one target structure prior to automatic rotation of the volume to a pre-defined orientation, in accordance with various embodiments.

FIG. 6 is an exemplary display 700 of biplane images 704, 706 and a rendering of an acquired volume 710 of the at least one target structure 712 prior to automatic rotation of the volume 710 to a pre-defined orientation, in accordance with various embodiments. Referring to FIG. 6, the display 700 comprises an image display portion 702 comprising biplane ultrasound images 704, 706 and a rendered ultrasound volume 710 of the region of interest (e.g., 408, 606 from FIGS. 3 and 5) surrounding the selected target structure 712. The rendered ultrasound volume 710 of the region of interest includes the selected target structure 712, such as a left atrial appendage (LAA), and surrounding structures 718, such as pulmonary valves (PVs). The selected target structure 712 comprises a shape having a major axis 714 and minor axis 716, which may be used by a volume rotation processor 170, along with the locations of surrounding anatomical structures 718, to rotate the ultrasound volume 710 to a pre-defined orientation. In various embodiments, the ultrasound volume 710 (i.e., prior to rotation) may not be displayed.

Referring again to FIG. 1, the signal processor 132 may include a volume rotation processor 170 that comprises suitable logic, circuitry, interfaces and/or code that may be operable to rotate the ultrasound volume 710 to a pre-defined orientation, render the rotated ultrasound volume, and cause a display system 134 to present the rotated and rendered ultrasound volume (i.e., second ultrasound image acquisition). For example, the volume rotation 170 processor may configured to rotate the ultrasound volume 710 based on the estimated pose information from the pose estimation processor 160 and a pre-defined orientation. The pre-defined orientation may correspond with a standard orientation from echocardiography guidelines and/or any suitable pre-defined orientations from other guidelines, settings, and/or configurations. The volume rotation processor 170 may, for example, calculate a rotation angle and rotation amount to transform the volume from the estimated pose to the pre-defined orientation. The volume rotation processor 170 may reference the major axis 714 and/or minor axis 716 of the shape of the target structure 712 and the location information for the surrounding structure 718 in the estimated pose with reference to the pre-defined orientation information to calculate and provide the rotation amount and rotation angle to transform the ultrasound volume to the pre-defined orientation. The volume rotation processor 170 may be configured to render and cause a display system 134 to present the rotated and rendered ultrasound volume.

Figure 7:
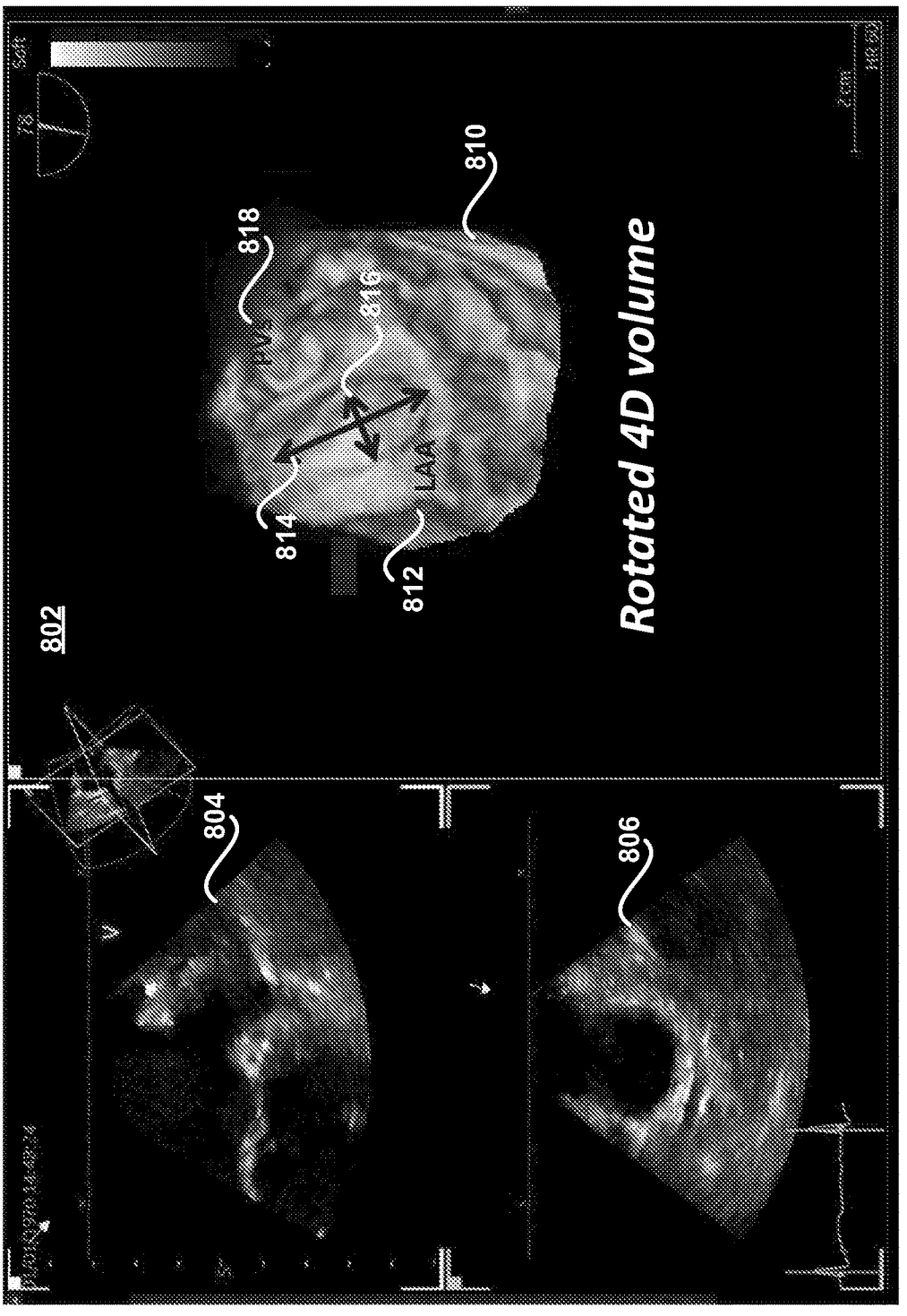
FIG. 7 is an exemplary display of biplane images and a rendering of an acquired volume of the at least one target structure after automatic rotation of the volume to a pre-defined orientation, in accordance with various embodiments.

FIG. 7 is an exemplary display 800 of biplane images 804, 806 and a rendering of an acquired volume 710 of the at least one target structure 812 after automatic rotation of the volume to a pre-defined orientation, in accordance with various embodiments. Referring to FIG. 7, the display 800 comprises an image display portion 802 comprising biplane ultrasound images 804, 806 and a rotated (e.g., from 710 in FIG. 6) and rendered ultrasound volume 810 of the region of interest (e.g., 408, 606 from FIGS. 3 and 5) surrounding the selected target structure 812. The rotated and rendered ultrasound volume 810 of the region of interest includes the selected target structure 812, such as a left atrial appendage (LAA), and surrounding structures 818, such as pulmonary valves (PVs). The selected target structure 812 comprises a shape having a major axis 814 and minor axis 816, rotated by the volume rotation processor 170 from the major axis 714 and minor axis 716 of the volume at the estimated pose 710. In various embodiments, the major axis 814 and minor axis 816 may not be displayed.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present 2D ultrasound images 304, biplane ultrasound images 404, 406, 504, 506, 604, 606, biplane ultrasound slices extracted from 3D/4D volumes 704, 706, 804, 806, rendered 3D/4D volumes 710, 810, selectable target structures 312, 514, 614, second ultrasound image acquisition initiating buttons 412, 518, 618, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores 2D ultrasound images 304, biplane ultrasound images 404, 406, 504, 506, 604, 606, biplane ultrasound slices extracted from 3D/4D volumes 704, 706, 804, 806, rendered 3D/4D volumes 710, 810, instructions for automatically detecting and tracking selected target structures and other anatomical structures, instructions for causing a display system 134 to present regions of interest 308, 508, 608 surrounding selected target structures and other anatomical structures, instructions for modifying region of interest positions and/or sizes, instructions for redefining a region of interest to include multiple regions of interest and/or exclude non-selected regions of interest, instructions for triggering a second ultrasound image acquisition (e.g., 3D/4D volume acquisition), instructions for estimating a pose of a target structure within an acquired volume, instructions for calculating a rotation of a volume from an estimated pose to a pre-defined orientation, pre-defined orientations, and/or instructions for rendering ultrasound volumes, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 210 may comprise suitable logic, circuitry, interfaces and/or code that may be operable to train the neurons of the deep neural network(s) (e.g., artificial intelligence model(s)) inferenced (i.e., deployed) by the structure detection processor 140 and/or pose estimation processor 160. For example, the artificial intelligence model inferenced by the structure detection processor 140 may be trained to automatically identify anatomical structures depicted in an ultrasound image and/or volume using database(s) 220 of classified ultrasound images and/or volumes of anatomical structures. As another example, the artificial intelligence model inferenced by the pose estimation processor 160 may be trained to automatically identify selected target structures, surrounding structures, target structure shapes, major/minor axes of target structures, and the like depicted in an ultrasound volume using database(s) 220 of classified ultrasound volumes of possible target structures.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms.

FIG. 8 is a flow chart 900 illustrating exemplary steps 902-920 that may be utilized for automatically acquiring and rotating an ultrasound volume 710, 810 based on a localized target structure 408, in accordance with various embodiments. Referring to FIG. 8, there is shown a flow chart 900 comprising exemplary steps 902 through 920. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 902, a signal processor 132 of the ultrasound system 100 may be configured to receive a user input selecting a target structure 312. For example, a structure detection processor 140 may be configured to receive a user input selecting a target structure 312, such as a left atrial appendage (LAA), via an interface 310 displaying a list of one or more selectable anatomical structures 312. The structure detection processor 140 may initiate a first ultrasound image acquisition in response to the selection of a target structure 312.

At step 904, an ultrasound probe 104 of an ultrasound system 100 performs a first ultrasound image acquisition. For example, the ultrasound probe 104 may be operable to acquire 2D ultrasound images, biplane ultrasound images 404, 406, 504, 506, 604, 606, 3D/4D volumes 710, 810, and/or any suitable ultrasound images. The acquired ultrasound images 404, 406, 504, 506, 604, 606 and/or volumes 710, 810 of the first ultrasound image acquisition may be provided to the structure detection processor 140 and/or stored at archive 138 and/or any suitable computer readable medium.

At step 906, the signal processor 132 of the ultrasound system 100 automatically detects and tracks the target structure 312 in the first ultrasound image acquisition. For example, the structure detection processor 140 may be configured to analyze acquired ultrasound images 404, 406 and/or volumes to detect a presence and location of the selected target structure 312 in the ultrasound images 404, 406, 504, 506, 604, 606 and/or volumes 710, 810. The structure detection processor 140 may include, for example, image analysis algorithms, one or more deep neural networks (e.g., a convolutional neural network such as u-net) and/or may utilize any suitable form of image analysis techniques, artificial intelligence, or machine learning processing functionality configured to detect and localize anatomical structures in ultrasound images and/or volumes. The detected and localized target structure 312 may be provided by the structure detection processor 140 to the region of interest processor 150. Additionally and/or alternatively, the detected and localized target structure 312 may be stored at archive 138 and/or any suitable computer readable medium.

At step 908, the signal processor 132 of the ultrasound system 100 presents the first ultrasound image acquisition 404, 406 with a region of interest 408 surrounding the target structure 312 at a display system 134. For example, a region of interest processor 150 of the signal processor 132 may be configured to cause a display system 134 to present the first ultrasound image acquisition 404, 406 with a region of interest 408 surrounding a selected target structure 312 detected and localized by the structure detection processor 140. The region of interest processor 150 may be configured to receive from the structure detection processor 140, or retrieve from the archive 138 and/or any suitable data storage medium, the identity and location of a selected target structure 312. The region of interest processor 150 may be configured to identify the localized selected target structure by overlaying a bounding box, colorizing pixels, and/or any suitable identification technique.

At step 910, the signal processor 132 of the ultrasound system 100 determines whether a modification to the region of interest 408 has been received from a user input device 130.

At step 912, the signal processor 132 of the ultrasound system 100 receives a modification to the region of interest 408. For example, the region of interest processor 150 may be configured to receive an instruction to modify the region of interest 408. As an example, in response to the region of interest processor 150 causing the display system 134 to present the first ultrasound image acquisition 404, 406 with the region of interest 408 surrounding a selected target structure 312, an ultrasound operator may provide an input via the user input device 130 and/or touchscreen display 130, 134 to modify a size and/or location of the displayed region of interest 408. The process 900 then returns to step 908 for the region of interest processor 150 to cause the display system 134 to present the first ultrasound image acquisition 404, 406 with the modified region of interest 408 surrounding a selected target structure 312.

At step 914, the signal processor 132 of the ultrasound system 100 may cause the ultrasound probe 104 to perform a second ultrasound image acquisition of the region of interest 408 to acquire a volume 710, 810. For example, the region of interest processor 150 may be configured to initiate a second ultrasound image acquisition of the region of interest 408 automatically and/or in response to a user input. As an example, the region of interest processor 150 may automatically initiate the second ultrasound image acquisition by the ultrasound probe 104 if a user input is not received to modify the position and/or size of the region of interest 408 in a predetermined period of time. As another example, the region of interest processor 150 may be configured to initiate the second ultrasound image acquisition by the ultrasound probe 104 in response to a user input. In addition, the region of interest processor 150 may be configured to initiate the second ultrasound image acquisition by the ultrasound probe 104 in response to a predetermined period of time expiring after the region of interest 408 has been modified and/or in response to a user input after the region of interest 408 has been modified. The ultrasound probe 104 may be operable to acquire the second ultrasound image acquisition, which is a volume acquisition. The acquired ultrasound volumes 710, 810 of the second ultrasound image acquisition may be provided to a pose estimation processor 160 of the signal processor 132 and/or stored at archive 138 and/or any suitable computer readable medium.

At step 916, the signal processor 132 of the ultrasound system 100 may estimate a pose of the target structure 712 within the ultrasound volume 710. For example, a pose estimation processor 160 of the signal processor 132 may be configured to estimate a pose of the target structure 712 within the second ultrasound image acquisition 710 (e.g., 3D/4D volume). As an example, the post estimation processor 160 may perform image segmentation and/or any suitable image identification techniques to estimate a pose of the target structure 712 depicted in the second ultrasound image acquisition 710. The pose estimation processor 160 may be configured to segment and/or otherwise identify the selected target structure 712 within the ultrasound volume 710. In this regard, the pose estimation processor 160 may include, for example, image analysis algorithms, artificial intelligence algorithms, one or more deep neural networks (e.g., a convolutional neural network such as u-net) and/or may utilize any suitable form of artificial intelligence image analysis techniques or machine learning processing functionality configured to provide segmentation of selected target structure(s) 712 and/or any suitable anatomical structure 718. The pose estimation processor 160 may be configured to store the estimated pose information at archive 138 and/or any suitable storage medium. The pose estimation processor 160 may be configured to provide a volume rotation processor 170 of the signal processor 132 with the estimated pose information. The estimated pose information may comprise, for example, location and boundaries of anatomical structures 712, 718, shape of anatomical structures 712, 718, major/minor axis information 714, 716, and the like.

At step 918, the signal processor 132 of the ultrasound system 100 may calculate a rotation of the ultrasound volume from the estimated pose 710 to a pre-defined orientation 810 of the target structure 812. For example, a volume rotation processor 170 of the signal processor 132 may be configured to rotate the ultrasound volume 710 (i.e., second ultrasound image acquisition) to a pre-defined orientation 810. As an example, the volume rotation 170 processor may configured to rotate the ultrasound volume 710 based on the estimated pose information from the pose estimation processor 160 and a pre-defined orientation. The pre-defined orientation may correspond with a standard orientation from echocardiography guidelines and/or any suitable pre-defined orientations from other guidelines, settings, and/or configurations. The volume rotation processor 170 may, for example, calculate a rotation angle and rotation amount to transform the volume from the estimated pose 710 to the pre-defined orientation 810. The volume rotation processor 170 may reference the major axis 714 and/or minor axis 716 of the shape of the target structure 712 and the location information for the surrounding structure 718 in the estimated pose with reference to the pre-defined orientation to calculate and provide the rotation amount and rotation angle to transform the ultrasound volume 710 to the pre-defined orientation 810.

At step 920, the signal processor 132 of the ultrasound system 100 may cause the display system 134 to present a rendering of the volume 810 automatically rotated to the pre-defined orientation. For example, the volume rotation processor 170 may be configured to render and cause a display system 134 to present the rotated and rendered ultrasound volume 810, at which point the process 900 ends.

FIG. 9 is a flow chart 1000 illustrating exemplary steps 1002-1018 that may be utilized for automatically acquiring and rotating an ultrasound volume 710, 810 based on a localized target structure 608, in accordance with various embodiments. Referring to FIG. 9, there is shown a flow chart 1000 comprising exemplary steps 1002 through 1018. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 1002, an ultrasound probe 104 of an ultrasound system 100 performs a first ultrasound image acquisition. For example, the ultrasound probe 104 may be operable to acquire 2D ultrasound images, biplane ultrasound images 404, 406, 504, 506, 604, 606, 3D/4D volumes 710, 810, and/or any suitable ultrasound images. The acquired ultrasound images 404, 406, 504, 506, 604, 606 and/or volumes 710, 810 of the first ultrasound image acquisition may be provided to the structure detection processor 140 and/or stored at archive 138 and/or any suitable computer readable medium.

At step 1004, a signal processor 132 of the ultrasound system 100 automatically detects and tracks one or more anatomical structures in the first ultrasound image acquisition. For example, a structure detection processor 140 of the signal processor 132 may be configured to analyze the ultrasound images 404, 406, 504, 506, 604, 606 and/or volumes 710, 810 of the first ultrasound image acquisition to detect and localize all anatomical structures present in the ultrasound images 404, 406, 504, 506, 604, 606 and/or volumes 710, 810. The structure detection processor 140 may include, for example, image analysis algorithms, one or more deep neural networks (e.g., a convolutional neural network such as u-net) and/or may utilize any suitable form of image analysis techniques, artificial intelligence, or machine learning processing functionality configured to detect and localize anatomical structures in ultrasound images and/or volumes. The detected and localized anatomical structures may be provided by the structure detection processor 140 to the region of interest processor 150. Additionally and/or alternatively, the detected and localized anatomical structures may be stored at archive 138 and/or any suitable computer readable medium.

At step 1006, the signal processor 132 of the ultrasound system 100 causes a display system 134 to present the first ultrasound image acquisition 504, 506 with a region of interest 508 surrounding each of the one or more anatomical structures. For example, a region of interest processor 150 of the signal processor may be configured to cause a display system 134 to present a first ultrasound image acquisition 504, 506 with regions of interest 508 surrounding all of the anatomical structures detected and localized by the structure detection processor 140 at step 1004. As an example, the region of interest processor 150 may be configured to receive from the structure detection processor 140, or retrieve from the archive 138 and/or any suitable data storage medium, the identity and location of all of the detected anatomical structures. The region of interest processor 150 may be configured to identify the localized anatomical structures by overlaying a bounding box, colorizing pixels, and/or any suitable identification technique. The first ultrasound image acquisition having the identified region(s) of interest may include a 2D image 304, 2D biplane images 404, 406, 2D biplane image slices extracted from a volume 504, 506, 604, 606, a rendered volume 710, 810, and/or any suitable ultrasound image and/or volume rendering (i.e., 2D projection of 3D/4D volume image data).

At step 1008, the signal processor 132 of the ultrasound system 100 may receive a user input selecting at least one target structure corresponding to at least one of the one or more anatomical structures. For example, in response to the region of interest processor 150 causing the display system 134 to present the first ultrasound image acquisition 504, 506 with the regions of interest 508 surrounding each of the localized anatomical structures at step 1006, an ultrasound operator may provide an input via the user input device 130 and/or touchscreen display 130, 134 to select one or more of the anatomical structures 508, 514, 614.

At step 1010, the signal processor 132 of the ultrasound system 100 may redefine the region of interest 608 to surround the selected at least one target structure 508, 514, 614. For example, the region of interest processor 150 may be configured to redefine the region of interest 608 in response to a user input selecting one or more of the regions of interest 508 and/or anatomical structures 514, 614 identified in the first ultrasound image acquisition 504, 506, 604, 606 at step 1008. The region of interest processor 150 may be configured to redefine the regions of interest 508 corresponding to the selected anatomical structures 508, 514, 614 to form a single region of interest 608 surrounding the selected anatomical structures 508, 514, 614.

At step 1012, the signal processor 132 of the ultrasound system 100 may cause the ultrasound probe 104 to perform a second ultrasound image acquisition of the region of interest 608 to acquire a volume 710, 810. For example, the region of interest processor 150 may be configured to initiate a second ultrasound image acquisition of the region of interest 608 automatically and/or in response to a user input. As an example, the region of interest processor 150 may automatically initiate the second ultrasound image acquisition by the ultrasound probe 104 if a user input is not received to select more or fewer regions of interest 508, 614, 616 to further redefine the region of interest 608 in a predetermined period of time. As another example, the region of interest processor 150 may be configured to initiate the second ultrasound image acquisition by the ultrasound probe 104 in response to a user input 618. The ultrasound probe 104 may be operable to acquire the second ultrasound image acquisition, which is a volume acquisition. The acquired ultrasound volumes 710, 810 of the second ultrasound image acquisition may be provided to a pose estimation processor 160 of the signal processor 132 and/or stored at archive 138 and/or any suitable computer readable medium.

At step 1014, the signal processor 132 of the ultrasound system 100 may estimate a pose of the target structure 712 within the ultrasound volume 710. For example, a pose estimation processor 160 of the signal processor 132 may be configured to estimate a pose of the target structure 712 within the second ultrasound image acquisition 710 (e.g., 3D/4D volume). As an example, the post estimation processor 160 may perform image segmentation and/or any suitable image identification techniques to estimate a pose of the target structure 712 depicted in the second ultrasound image acquisition 710. The pose estimation processor 160 may be configured to segment and/or otherwise identify the selected target structure 712 within the ultrasound volume 710. In this regard, the pose estimation processor 160 may include, for example, image analysis algorithms, artificial intelligence algorithms, one or more deep neural networks (e.g., a convolutional neural network such as u-net) and/or may utilize any suitable form of artificial intelligence image analysis techniques or machine learning processing functionality configured to provide segmentation of selected target structure(s) 712 and/or any suitable anatomical structure 718. The pose estimation processor 160 may be configured to store the estimated pose information at archive 138 and/or any suitable storage medium. The pose estimation processor 160 may be configured to provide a volume rotation processor 170 of the signal processor 132 with the estimated pose information. The estimated pose information may comprise, for example, location and boundaries of anatomical structures 712, 718, shape of anatomical structures 712, 718, major/minor axis information 714, 716, and the like.

At step 1016, the signal processor 132 of the ultrasound system 100 may calculate a rotation of the ultrasound volume from the estimated pose 710 to a pre-defined orientation 810 of the target structure 812. For example, a volume rotation processor 170 of the signal processor 132 may be configured to rotate the ultrasound volume 710 (i.e., second ultrasound image acquisition) to a pre-defined orientation 810. As an example, the volume rotation 170 processor may configured to rotate the ultrasound volume 710 based on the estimated pose information from the pose estimation processor 160 and a pre-defined orientation. The pre-defined orientation may correspond with a standard orientation from echocardiography guidelines and/or any suitable pre-defined orientations from other guidelines, settings, and/or configurations. The volume rotation processor 170 may, for example, calculate a rotation angle and rotation amount to transform the volume from the estimated pose 710 to the pre-defined orientation 810. The volume rotation processor 170 may reference the major axis 714 and/or minor axis 716 of the shape of the target structure 712 and the location information for the surrounding structure 718 in the estimated pose with reference to the pre-defined orientation information to calculate and provide the rotation amount and rotation angle to transform the ultrasound volume 710 to the pre-defined orientation 810.

At step 1018, the signal processor 132 of the ultrasound system 100 may cause the display system 134 to present a rendering of the volume 810 automatically rotated to the pre-defined orientation. For example, the volume rotation processor 170 may be configured to render and cause a display system 134 to present the rotated and rendered ultrasound volume 810, at which point the process 1000 ends.

Aspects of the present disclosure provide a method 900, 1000 and system 100 for automatically acquiring and rotating an ultrasound volume 710, 810 based on a localized target structure 408, 508, 608. In accordance with various embodiments, the method 900, 1000 may comprise performing 904, 1002, by an ultrasound probe 104 of an ultrasound system 100, a first ultrasound image acquisition 404, 406, 504, 506, 604, 606. The method 900, 1000 may comprise automatically detecting and tracking 906, 1004, by at least one processor 132, 140 of the ultrasound system 100, one or more anatomical structures 312, 514, 614 in the first ultrasound image acquisition 404, 406, 504, 506, 604, 606. The method 900, 1000 may comprise causing 908, 1006, by the at least one processor 132, 150, a display system 134 to present a region of interest 408, 508, 608 surrounding each of the one or more anatomical structures 312, 514, 614 in the first ultrasound image acquisition 404, 406, 504, 506, 604, 606. The method 900, 1000 may comprise performing 914, 1012, by the ultrasound probe 104, a second ultrasound image acquisition 710, 810 of the region of interest 408, 508, 608 to acquire a volume 710, 810. The method 900, 1000 may comprise estimating 916, 1014, by the at least one processor 132, 160, a pose 714, 716 of the one or more anatomical structures 712, 718, 812, 818 within the volume 710, 810. The method 900, 1000 may comprise calculating 918, 1016, by the at least one processor 132, 179, a rotation of the volume 710, 810 from the estimated pose 714, 716 to a pre-defined orientation 814, 816 of the one or more anatomical structures 712, 718, 812, 818. The method 900, 1000 may comprise causing 920, 1018, by the at least one processor 132, 170, the display system 134 to present a rendering of the volume 710, 810 automatically rotated to the pre-defined orientation 814, 816.

In an exemplary embodiment, the method 900, 1000 comprises receiving 912, by the at least one processor 132, 150, a user input to modify the region of interest 408 presented at the display system 134. In a representative embodiment, the second ultrasound image acquisition 710, 810 is automatically performed 914, 1012 in response to not receiving a user input 910 to modify the region of interest 408 presented at the display system 134 within a predetermined period of time. In various embodiments, the method 900, 1000 comprises receiving 902, by the at least one processor 132, 140, a user input selecting a target structure 312. The one or more anatomical structures is the selected target structure 312. The automatically detecting and tracking 906 the one or more anatomical structures is performed based on the user input 902 selecting the target structure 312. In certain embodiments, the first ultrasound image acquisition 404, 406, 504, 506, 604, 606 is two-dimensional biplane images 404, 406, 504, 506, 604, 606. In an exemplary embodiment, the performing 904 the first ultrasound image acquisition 404, 406, 504, 506, 604, 606 is performed in response to the receiving 902 the user input selecting the target structure 312. In a representative embodiment, the method 900, 1000 comprises receiving 1008, by the at least one processor 132, 150, a user input selecting at least one target structure 508, 514, 614 in response to the display system 134 presenting the region of interest 508 surrounding each of the one or more anatomical structures in the first ultrasound image acquisition 404, 406, 504, 506, 604, 606. The at least one target structure 508, 514, 614 corresponds with at least one of the region of interest 508 surrounding each of the one or more anatomical structures in the first ultrasound image acquisition 404, 406, 504, 506, 604, 606. The method 900, 1000 comprises redefining 1010 the region of interest 608 to surround the selected at least one target structure 508, 514, 614. In various embodiments, each of the region of interest 508 surrounding each of the one or more anatomical structures in the first ultrasound image acquisition 404, 406, 504, 506, 604, 606 presented at the display system 134 is selectable as the at least one target structure 508, 514, 614. In certain embodiments, the method 900, 1000 comprises causing 1006, by the at least one processor 132, 150, the display system 134 to present an activatable button 514, 614 corresponding with each of the one or more anatomical structures 508, 514, 614 in the first ultrasound image acquisition 404, 406, 504, 506, 604, 606. The receiving 1008 the user input selecting the at least one target structure 508, 514, 614 is provided by selecting at least one of the activatable button 514, 614. In an exemplary embodiment, the first ultrasound image acquisition 404, 406, 504, 506, 604, 606 is a volume acquisition.

Various embodiments provide a system 100 for automatically acquiring and rotating an ultrasound volume 710, 810 based on a localized target structure 408, 508, 608. The system 100 may comprise an ultrasound probe 104, at least one processor 132, 140, 150, 160, 170 and a display system 134. The ultrasound probe 104 may be configured to perform a first ultrasound image acquisition 404, 406, 504, 506, 604, 606. The ultrasound probe 104 may be configured to perform a second ultrasound image acquisition 710, 810 of a region of interest 408, 508, 608 to acquire a volume 710, 810. The at least one processor 132, 140 may be configured to automatically detect and track one or more anatomical structures 312, 514, 614 in the first ultrasound image acquisition 404, 406, 504, 506, 604, 606. The at least one processor 132, 150 may be configured to cause a display system 134 to present the region of interest 408, 508, 608 surrounding each of the one or more anatomical structures 312, 514, 614 in the first ultrasound image acquisition 404, 406, 504, 506, 604, 606. The at least one processor 132, 160 may be configured to estimate a pose 714, 716 of the one or more anatomical structures 712, 718, 812, 818 within the volume 710, 810. The at least one processor 132, 170 may be configured to calculate a rotation of the volume 710, 810 from the estimated pose 714, 716 to a pre-defined orientation 814, 816 of the one or more anatomical structures 712, 718, 812, 818. The display system 134 may be configured to present the region of interest 408, 508, 608 surrounding each of the one or more anatomical structures 312, 514, 614 in the first ultrasound image acquisition 404, 406, 504, 506, 604, 606. The display system 134 may be configured to present a rendering of the volume 710, 810 automatically rotated to the pre-defined orientation 814, 816.

In a representative embodiment, the at least one processor 132, 150 is configured to receive a user input to modify the region of interest 408 presented at the display system 134. In various embodiments, the second ultrasound image acquisition 710, 810 is automatically performed in response to the at least one processor 132, 150 not receiving a user input to modify the region of interest 408 presented at the display system 134 within a predetermined period of time. In certain embodiments, the at least one processor 132, 140 is configured to receive a user input selecting a target structure 312. The one or more anatomical structures 312 is the selected target structure 312. The at least one processor 132, 140 is configured to automatically detect and track the one or more anatomical structures 312 based on the user input selecting the target structure 312. In an exemplary embodiment, the first ultrasound image acquisition 404, 406, 504, 506, 604, 606 is two-dimensional biplane images 404, 406, 504, 506, 604, 606. In a representative embodiment, the ultrasound probe 104 is configured to perform the first ultrasound image acquisition 404, 406, 504, 506, 604, 606 in response to the user input selecting the target structure 312. In various embodiments, the at least one processor 132, 150 is configured to receive a user input selecting at least one target structure 508, 514, 614 after the display system 134 presents the region of interest 508 surrounding each of the one or more anatomical structures in the first ultrasound image acquisition 404, 406, 504, 506, 604, 606. The at least one target structure 508, 514, 614 corresponds with at least one of the region of interest 508 surrounding each of the one or more anatomical structures in the first ultrasound image acquisition 404, 406, 504, 506, 604, 606. The at least one processor 132, 150 is configured to redefine the region of interest 608 to surround the selected at least one target structure 508, 514, 614. In certain embodiments, each of the region of interest 508 surrounding each of the one or more anatomical structures in the first ultrasound image acquisition 404, 406, 504, 506, 604, 606 presented at the display system 134 is selectable as the at least one target structure 508, 514, 614. In an exemplary embodiment, the display system 134 is configured to present an activatable button 514, 614 corresponding with each of the one or more anatomical structures 508, 514, 614 in the first ultrasound image acquisition 404, 406, 504, 506, 604, 606. The user input selecting the at least one target structure 508, 514, 614 is provided via at least one of the activatable button 514, 614. In a representative embodiment, the first ultrasound image acquisition 404, 406, 504, 506, 604, 606 is a volume acquisition.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z). (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for automatically acquiring and rotating an ultrasound volume based on a localized target structure.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
performing, by an ultrasound probe of an ultrasound system, a first ultrasound image acquisition;
automatically detecting and tracking, by at least one processor of the ultrasound system, one or more anatomical structures in the first ultrasound image acquisition;
causing, by the at least one processor, a display system to present a region of interest surrounding each of the one or more anatomical structures in the first ultrasound image acquisition;
performing, by the ultrasound probe, a second ultrasound image acquisition of the region of interest to acquire volume image data of a target structure selected from a plurality of selectable target structures of the first ultrasound image acquisition, wherein each of the plurality of selectable target structures is associated with a pre-defined orientation;
estimating, by the at least one processor, a pose of the selected target structure within the volume image data;
calculating, by the at least one processor, a rotation of the volume image data from the estimated pose to the pre-defined orientation associated with the selected target structure; and
causing, by the at least one processor, the display system to present a rendering of the volume image data automatically rotated to the pre-defined orientation.

2. The method of claim 1, comprising receiving, by the at least one processor, a user input to modify the region of interest presented at the display system.

3. The method of claim 1, wherein the second ultrasound image acquisition is automatically performed in response to not receiving a user input to modify the region of interest presented at the display system within a predetermined period of time.

4. The method of claim 1, wherein the first ultrasound image acquisition is a volume acquisition.

5. The method of claim 1, comprising receiving, by the at least one processor, a user input selecting the target structure, wherein the one or more anatomical structures is the selected target structure, and wherein the automatically detecting and tracking the one or more anatomical structures is performed based on the user input selecting the target structure.

6. The method of claim 5, wherein the first ultrasound image acquisition is two-dimensional biplane images.

7. The method of claim 6, wherein the performing the first ultrasound image acquisition is performed in response to the receiving the user input selecting the target structure.

8. The method of claim 1, comprising:
receiving, by the at least one processor, a user input selecting the target structure in response to the display system presenting the region of interest surrounding each of the one or more anatomical structures in the first ultrasound image acquisition, wherein the target structure corresponds with at least one of the region of interest surrounding each of the one or more anatomical structures in the first ultrasound image acquisition, and redefining the region of interest to surround the selected target structure.

9. The method of claim 8, wherein each of the region of interest surrounding each of the one or more anatomical structures in the first ultrasound image acquisition presented at the display system is selectable as the target structure.

10. The method of claim 8, comprising causing, by the at least one processor, the display system to present an activatable button corresponding with each of the one or more anatomical structures in the first ultrasound image acquisition, wherein the receiving the user input selecting the target structure is provided by selecting at least one of the activatable button.

11. An ultrasound system comprising:
an ultrasound probe configured to:
perform a first ultrasound image acquisition;
perform a second ultrasound image acquisition of a region of interest to acquire volume image data of a target structure selected from a plurality of selectable target structures of the first ultrasound image acquisition, wherein each of the plurality of selectable target structures is associated with a pre-defined orientation;
at least one processor configured to:
automatically detect and track one or more anatomical structures in the first ultrasound image acquisition;
cause a display system to present the region of interest surrounding each of the one or more anatomical structures in the first ultrasound image acquisition;
estimate a pose of the selected target structure within the volume image data; and
calculate a rotation of the volume image data from the estimated pose to the pre-defined orientation associated with the selected target structure; and
the display system configured to:
present the region of interest surrounding each of the one or more anatomical structures in the first ultrasound image acquisition; and
present a rendering of the volume image data automatically rotated to the pre-defined orientation.

12. The ultrasound system of claim 11, wherein the at least one processor is configured to receive a user input to modify the region of interest presented at the display system.

13. The ultrasound system of claim 11, wherein the second ultrasound image acquisition is automatically performed in response to the at least one processor not receiving a user input to modify the region of interest presented at the display system within a predetermined period of time.

14. The ultrasound system of claim 11, wherein the first ultrasound image acquisition is a volume acquisition.

15. The ultrasound system of claim 11, wherein:
the at least one processor is configured to receive a user input selecting the target structure,
the one or more anatomical structures is the selected target structure, and the at least one processor is configured to automatically detect and track the one or more anatomical structures based on the user input selecting the target structure.

16. The ultrasound system of claim 15, wherein the first ultrasound image acquisition is two-dimensional biplane images.

17. The ultrasound system of claim 16, wherein the ultrasound probe is configured to perform the first ultrasound image acquisition in response to the user input selecting the target structure.

18. The ultrasound system of claim 11, wherein:

the at least one processor is configured to receive a user input selecting the target structure after the display system presents the region of interest surrounding each of the one or more anatomical structures in the first ultrasound image acquisition, the target structure corresponds with at least one of the region of interest surrounding each of the one or more anatomical structures in the first ultrasound image acquisition, and the at least one processor is configured to redefine the region of interest to surround the selected target structure.

19. The ultrasound system of claim 18, wherein each of the region of interest surrounding each of the one or more anatomical structures in the first ultrasound image acquisition presented at the display system is selectable as the target structure.

20. The ultrasound system of claim 18, wherein the display system is configured to present an activatable button corresponding with each of the one or more anatomical structures in the first ultrasound image acquisition, the user input selecting the target structure is provided via at least one of the activatable button.

* * * * *